United States Patent [19]

Kranbuehl

[11] Patent Number: 4,723,908
[45] Date of Patent: Feb. 9, 1988

[54] DIELECTRIC PROBE; METHOD AND APPARATUS INCLUDING ITS USE

[76] Inventor: David E. Kranbuehl, 201 Harrison Ave., Williamsburg, Va. 23185

[21] Appl. No.: 729,459

[22] Filed: May 1, 1985

[51] Int. Cl.$^4$ .......................... F27B 9/40; G01R 27/26
[52] U.S. Cl. ...................................... 432/37; 324/61 P
[58] Field of Search ............... 361/301, 303, 305, 321, 361/322; 526/59, 60, 61; 324/61 P, 61 R; 432/36, 37, 43; 436/85

[56] References Cited

U.S. PATENT DOCUMENTS

| | | |
|---|---|---|
| 3,986,110 | 10/1976 | Overall et al. ...................... 324/61 P |
| 4,510,436 | 4/1985 | Raymond ........................... 324/61 P |
| 4,541,904 | 9/1985 | Lüder et al. ....................... 324/61 R |

Primary Examiner—Harry Tanner
Attorney, Agent, or Firm—William L. Krayer

[57] ABSTRACT

A dielectric probe for use with conventional frequency and time domain impedance analyzers comprises two chemically resistant electrodes deposited in an interdigitated pectinate configuration on particular non-conductive substrates, the spaces between the digits thereof being no greater than about 0.01 inch; methods and apparatus for monitoring and/or controlling chemical reactions, particularly polymerization reactions, in contact therewith, wherein the complex permittivity may be calculated over a wide range of frequencies and temperatures.

9 Claims, 3 Drawing Figures

DIELECTRIC PROBE; METHOD AND APPARATUS INCLUDING ITS USE

This invention was made with U.S. Government support under contract NAG 1-237 awarded by NASA. The Government has certain rights in this invention.

BACKGROUND OF THE INVENTION

This invention relates to apparatus and methods for measuring, monitoring and/or controlling the characteristics of a medium which may be contacted with a probe. The probe is designed for use with conventional frequency and time domain impedance analyzers.

Interest in the use of electrical measurements to characterize materials has existed for over fifty years. Many excellent books reviewing this literature have been written, i.e. Hedvig, P., *Dielectric Spectroscopy of Polymers*, John Wiley, New York, 1977; Hill, N., Vaughan, W., Price, A., and Davies, M., *Dielectric Properties and Molecular Behavior*, Van Nostrand Reinhold, New York, 1969; McCrum, N., Read, B., and Williams, G., *Anelastic and Dielectric Effects in Polymeric Solids*, John Wiley, London, 1967; North, A., J. of Polymer Science Symposium 50. 345-358, 1978; Wada, Y., *Dielectric and Related Molecular Processes* 3, 143-175, 1977; Karasz, F., *Dielectric Properties of Polymers*, Plenum Press, New York, 1972; Read, B. E. and Dean, G. D., *The Determination of Dynamic Properties of Polymers and Composites*, John Wiley, New York, 1978, and May, C. A., *Chemorheology of Thermosetting Polymers*, American Chemical Society Symposium Ser., 227, 1983. The extensive use of electrical measurements, primarily utilizing dielectric techniques, to characterize materials has led to a current interest in using electrical measurements to monitor cure processes in resins. The reason for this interest is that there are very few other techniques for convenient and continuous monitoring of the cure process through a wide range of resin viscosity, i.e. less than $10^2$ to more than $10^9$ poise.

Until the last several years, research on the use of electrical measurements has often fallen short of expectations. While reasons for this are in most cases complex, usually they were related to inadequate instrumentation, i.e. the use of instrumentation such as sensors not designed specifically for the purpose, failure to make measurements over a wide range of frequencies, not understanding the molecular basis for the signal in terms of dipolar and ionic phenomena, and lack of an integrated approach to interpret the electrical measurements in a manner correlatable to other chemical characterization measurements.

The effective and successful use of dynamic electrical measurements for cure cycle monitoring requires an extensive effort involving basic research on the chemistry of each resin or other medium using a variety of characterization techniques, which are then correlated with dynamic electrical measurements made over a wide range of frequencies. Only with this background information is it possible for electrical measurements to be most effectively used to monitor the cure process or other reaction and to provide the input for a complete mathematical processing model for quality assurance cure cycle monitoring as well as closed loop "smart" cure cycle control.

As indicated above, convenient and accurate measurements of electrical characteristics of chemicals undergoing chemical reactions have not been easily made in the past or utilized conventionally to monitor and/or correlate the chemical and physical characteristics of the reaction products with them. I have observed particularly that the complex permittivity of a polymerizing resin has a particular relationship to the progress of the polymerization reaction, but until now the art has not developed the apparatus and techniques necessary to exploit that relationship over the wide range of frequencies and the wide variation in the magnitude of the complex permittivity required for a useful correlation.

For example, a description of a rather elaborate system for controlling polymerization process variables is given in U.S. Pat. No. 4,448,943, but it utilizes a "slit die into which is incorporated a parallel plate capacitance cell" for the measuring device. While the parallel plate capacitance cell will provide a gross measurement of capacitance, it has certain disadvantages, compared to my planar interdigitated device including an inability to maintain a controlled spatial relationship between electrodes at the desirable small distances. More important, my method employs the capacitance and the conductance of the medium to first calculate the more useful complex permittivity. Golba and Hansen, in U.S. Pat. No. 4,448,943, do not utilize the complex permittivity of the reacting materials as I do.

Measurements through a wide range of frequencies are generally described in my article "Dynamic Dielectric Characterization of the Cure Process:LARC-160" (SAMPE Journal, July/August 1983, p. 18) and in my chapter "Electrical Methods of Characterization of Cure Processes in Resins" to be published in Developments in Reinforced Plastics-5 by Elsevier Publishers. However, many of the prior art dielectric or capacitance probes utilize either parallel plane electrodes or, if they are on the same plane, as mine are, they are either covered with insulation or the authors do not appreciate the importance of the dimension, geometry, and materials of construction as I have outlined. In this regard, the reader may be interested in reviewing Zurbrick et al U.S. Pat. No. 3,515,987 describing a dielectric probe employed illustratively as a moisture detector, Overall U.S. Pat. No. 3,873,927, also describing a "wet condition" detector, and Hanzawa et al U.S. Pat. No. 3,841,610, Geisselmann U.S. Pat. No. 3,777,257 and Burkhardt et al U.S. Pat. No. 4,057,823.

The Jung et al patent No. 4,296,630 shows a particularly clear illustration of an interdigitated pectinate configuration; however, the detector, being constructed to detect the presence or absence of a liquid, i.e. to detect the level to which the capacitor gauge is covered, is indifferent to the dimensions and material characteristics which are necessary to my purposes.

In most configurations of the prior art, the probe is in general a relatively massive and rigid structure. The configuration of electrodes is relatively or offhand constant. The particular materials used, the spacing of the electrodes, the width of the electrodes and the precision/reproducibility in the electrode pattern are not critical nor utilized as the purpose of these probes is generally to determine the presence or absence of a material or its proximity to the probe.

A number of workers in the art have employed field effect transistors and/or charge-flow transistors in probes or sensors to observe the electrical characteristics of various media. See, for example, Covington et al U.S. Pat. No. 4,437,969, Grudkowski et al 4,247,903, Janata et al U.S. Pat. No. 4,322,680, and a number of patents to Senturia and others, i.e. 4,317,084, 4,316,140, 4,209,796, 4,158,807, 4,236,121, and 4,423,371. A Senturia patent of particular interest is 4,352,059, showing, again, a configuration particularly for moisture measurements.

SUMMARY OF THE INVENTION

I have invented a probe adapted specially to monitor and control chemical reactions and particularly polymerizations when used with my apparatus and methods to follow or control the complex permittivity of the reaction media.

My probe is a thin, flat capacitor probe which comprises an array of straight or curved, usually parallel, electrode lines preferably in an interdigitated pectinate configuration. The electrode lines are conducting, preferably metallic, such as titanium, tungsten, gold, copper, platinum, palladium, chromium or combinations thereof, less than about 10 mils apart and less than 20 mils (0.02 inch) wide. The two arrays of lines form the two terminals of a capacitor. Rather than utilizing the common configuration of a capacitor consisting of plates in parallel planes with the material to be measured between the plates, my probe measures the capacitance between an array of lines, preferably on the same plane. The material to be measured is placed in contact with the array of lines. When a voltage is placed across the two electrically isolated arrays, the electric field between the lines passes up and through the material which is in contact with the probe. The probe utilizes the fringing effects of the electric field to measure the dielectric properties of the material placed against the side of the probe as well as the electric field which passes through the small amount of material which is directly between the lines. The array of lines is held stationary on the surface of a substrate comprising a low loss polymer film (such as Kapton), glass, ceramic, Al$_2$O$_3$, or other dielectric material with a low loss tangent, i.e. whose conductivity remains below about $10^{-7}$ ohm$^{-1}$ cm$^{-1}$ over the range of use (which may be from 0°–400° C)—that is, over a frequency range of one Hz to about 10 megahertz. The lines are preferably photo etched on the substrate which has had a thin metal film glued or deposited on its surface. The total thickness of the probe is preferably less than 100 mils.

The probe's geometry and design offer several advantages. A major advantage is that the material to be monitored or measured can easily be placed against the capacitor probe rather than having to position the material between capacitor plates. It is therefore ideal for monitoring the properties of thin films, coatings, and adhesives since it can measure their dielectric properties by looking at them from one side only. The probe can be used to measure very thin samples—samples which are of comparable thickness to the spacing between the lines, i.e., as thin as one millimeter or even less. The capacitor probe is ideal for monitoring the dielectric properties of laminates and adhesives because it can be inserted between the layers of the laminate or on its surface. Dielectric measurements are not affected by changes in laminate thickness which is often the case when the laminate is placed between the electrodes of the capacitor, as the probe's lines are bonded to the electric substrate.

The geometric reproducibility, dimensions, and stability of the electrodes and the use of a low loss, dependable substrate allow determination of the complex permittivity $\epsilon^* = \epsilon' - i\epsilon''$, an intensive property not just C and tan $\delta$. The dielectric probe's configuration also permits measurement of a material during curing of a resin or laminate over a wide temperature range (0° to 400° C.) while the material undergoes changes in its physical state, i.e., liquid to gel to rubber to glass to solid (SAMPE 28 608 [1983]). The probe is less sensitive to the problem of shrinkage and expansion of the material than capacitance monitors which utilize parallel-plane plates or electrodes. The probe is also ideal for measuring the dielectric properties of liquids, thin films, uncured resin-cloth composites ("prepregs"), rubbers, and gels with high viscosities as only the surface of the probe needs to be wetted.

In addition to a well-designed probe specially adapted for the purpose, there are three major areas which need to be addressed to effectively use electrical measurements to monitor a resin's cure process. The first is instrumentation. Major advances have been made in this area. A number of rapid, low noise automatic bridges which span up to six decades in frequency have been introduced commercially during the past few years. Suitable examples are the impedance analyzers sold by Hewlett-Packard, General Radio (Gen.Rad.), Tetrahedron and Fourier transform (time domain) spectrometers which may be custom built (see Mopsik Rev. Sci. Instrum. 55(1) January 1984). The electrical properties of individual resins vary greatly and may change by factors of $10^6$ or more during the cure process. Thus, the selection of instrumentation and its components should be designed and matched to a particular resin's properties, the use objectives, the operating conditions, plant processing constraints, software, etc.

A second major area, often representing over half of the problem, is interpreting and understanding the molecular basis of the electrical signal. Critical aspects of this problem include making rapid measurements over a wide range of frequencies and then correlating the molecular basis of the frequency dependence of the signal to the chemistry and physics of the resin system. Frequency dependent electrical measurements may be correlated to carbon-13 nuclear magnetic resonance, gel permeation chromatography, infrared spectroscopy, viscosity, ultrasonics and differential scanning calorimetry data.

The third aspect of the problem is integrating the chemical and flow information embedded in the complex electrical signal's magnitude and frequency dependence into the processing model used for quality assurance and/or closed loop "smart" cure cycle control. The development of processing models is an extensive subject which is also currently under development. See May, C. A., *Chemorheology of Thermosetting Polymers,* American Chemical Society Symposium Ser., 227, 1983.

Measurements of the electrical properties of a material are preferably made with an impedance analyzer. An impedance analyzer measures the opposition that the material presents to an alternating current in terms of the complex ratio of the voltage to the current.

$$Z^* = \frac{V(\omega)}{I(\omega)} \qquad (1)$$

where $Z^*$ is the complex impedance. The output of the analyzer is representative of the magnitude and time shift of the voltage relative to the current. Often the properties of the material and its impedance are conveniently represented by an equivalent circuit of a capacitor ($C_s$) and resistor ($R_s$) in series. In this case:

$$Z^* = R_s + \frac{1}{i\omega C_s} \quad (2)$$

Similarly, the properties of the material can be represented by an equivalent circuit of a resistor ($R_p$) and capacitor ($C_p$) in parallel, in which case:

$$\frac{1}{Z^*} = \frac{I(\omega)}{V(\omega)} = Y^* \quad (3)$$

$$Y^* = \frac{1}{R_p} + i\omega C_p = G_p + i\omega C_p$$

where $Y^*$ is the admittance and the reciprocal of the parallel resistance is the conductance $G_p$.

To describe the properties of a capacitor filled with a poorly conducting material a third notation may be used. In this notation the equivalent circuit is viewed as simply a capacitor with capacitance $C_o$ without the material and capacitance $C = \epsilon C_o$ with the material. The magnitude and time shift of the current with respect to the voltage is represented by the complex value of the material's permittivity $\epsilon^*$ where $\epsilon^* = \epsilon' - i\epsilon''$. Again from elementary circuit theory:

$$\frac{1}{Z^*} = \frac{I(\omega)}{V(\omega)} = i\omega \epsilon^* C_o = \epsilon'' \omega C_o + i\omega \epsilon' C_o \quad (4)$$

All of these representations are simply two parameter equivalent circuit representations describing the propogation of an electromagnetic field through a material. Given one pair of parameters, it is possible to re-express them in terms of another equivalent circuit pair.

The electrical conductance of resins is usually low and the capacitive properties are moderate to high. Therefore the resin's electrical properties should be expressed in terms of the third notation, the complex permittivity $\epsilon^*$ Furthermore, since polymeric materials are poor conductors, the term "dielectric properties" may be used in place of electrical properties.

Referring now to the drawings.

Figure 1:
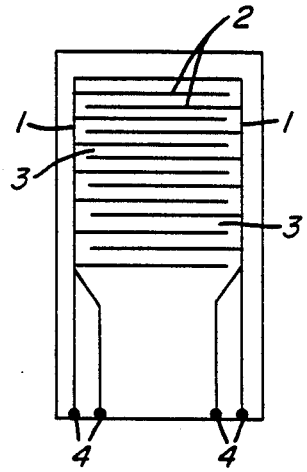
FIG. 1 is an enlarged more or less diagrammatic front view of a preferred form of my probe.

Referring to FIG. 1, a preferred probe comprises a pair of electrodes (1) each having fingers (2) in a pectinate configuration and which are interdigitated. The drawing is intended only to illustrate the geometric relationships and not the true dimensions. Preferably between about 100 and 200 fingers or lines (2) less than about 0.02 inch wide are placed with spaces (3) between them no greater than about 0.01 inch. The number of fingers may vary as a function of the frequency to be used, but in general should be at least 33 per inch. Each electrode (1) may have two terminals (4) for connection with an appropriate bridge or analyzer if it uses a four-terminal measurement. The electrodes (1) may be made of copper or preferably, for many of the uses I visualize, are of a more chemical-resistant conductor such as gold, platinum, chromium, titanium, tungsten, palladium, or combinations thereof. They are affixed to the substrate (5) in a known manner such as by vapor deposition and/or a suitable adhesive, and may be etched from a continuous layer, also in a known manner. Chemical resistance is of course a relative and a subjective matter; the choice of electrode materials will depend on the medium to be measured. Many of the applications of my probe are one-time uses and the probe may be discarded after one use.

The substrate (5) is important and plays a significant role in my invention; it should comprise a material which has a low dielectric loss tangent, as explained above, over the range of temperatures and frequencies used, and should have a dependable, (e.g. stable) capacitance curve, exhibiting little or no hysteresis through the range of 1 hertz to 10 megahertz at the temperatures of use. Its dielectric permittivity should be less than 13, with reproducible change over the frequency of use. The dielectric characteristics of the substrate should be known to the user, as is evident from the formulas and calculations throughout. For example, where an addition cross-linking system (or reaction) is to be monitored, typically a probe having a loss tangent less than 0.001, and an equivalent parallel plate replaceable capacitance of more than 10 pf over the temperature and frequency range of use is required.

Figure 2:
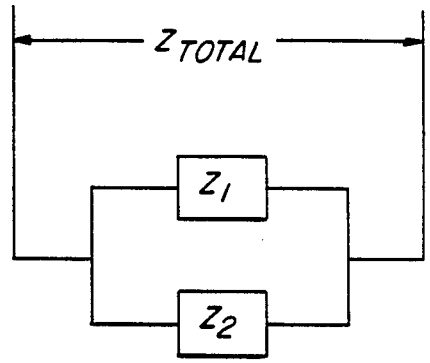
FIG. 2 is a conceptual diagram of a preferred system for monitoring the complex permittivity of a reaction mass.

In FIG. 2, $Z_{total}$ represents the overall impedance measurement which may be made by a dielectric bridge or analyzer where a probe of FIG. 1 is placed in contact with a material to be measured having an impedance $Z_2$. The impedance of the substrate of the probe is represented by $Z_1$; because of its low value it will not mask the effect of $Z_2$ on $Z_{total}$.

Figure 3:
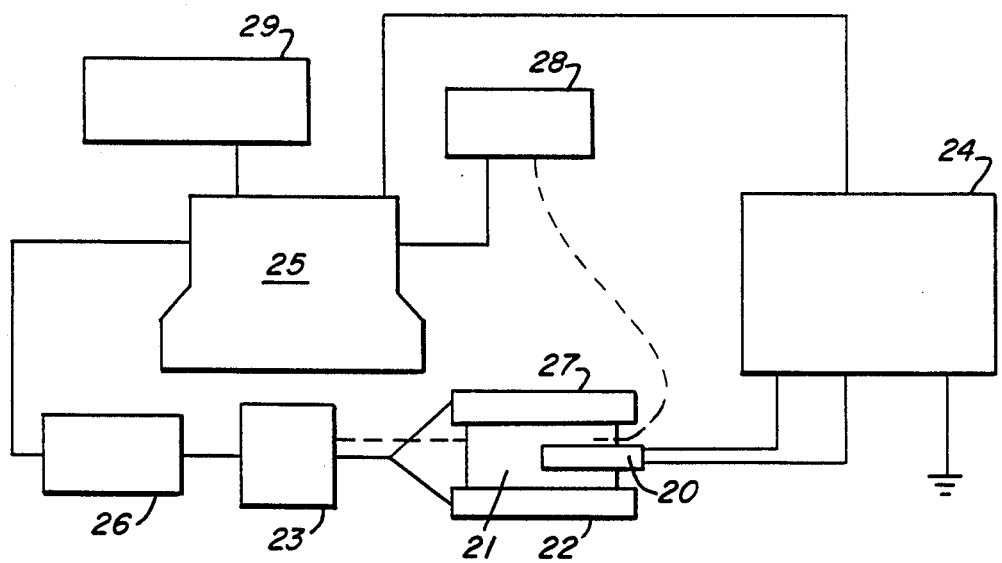
FIG. 3 is a simplified block diagram of a preferred system for controlling the time-temperature cycle of a polymerization reaction.

Referring to FIG. 3, the probe (20) similar to FIG. 1 is laid on or imbedded in a polymeric mold medium (21) contained by a heater (22), which is controlled by temperature controller (23). An iron-Constantan thermocouple (27) is attached directly to the mold and the temperature is measured by a Keithley 179 TRMS Digital Multimeter (28). The probe inputs to the dielectric bridge (24) yield an output representative of complex permittivity according to the formulations discussed above; the computer (25) monitors, records, and analyzes the frequency dependence of the complex permittivity. Based on this information and predetermined quality assurance criteria from other samples and runs, the computer passes a signal to the digital-to-analog converter (26), which is the input to the temperature controller and thereby controls on-line the time temperature profile of the medium (21).

Operation of the apparatus typically is as follows: The time-temperature profile of the mold is controlled by a program in the computer based on pre-determined correlations thereof to the desired properties of the product. The layup may consist of a number of layers of Kapton to insulate the probe from the metal mold, a probe which can be inserted directly between layers of polymer resin and further layers of Kapton between this and the mold top. Measurements of capacitance ($C_p$) and conductance ($G_p$) at frequencies from 5 to $5 \times 10^6$ Hz are taken of the resin in contact with the probe at regular intervals during the cure cycle and stored on a computer disk. The complex permittivity is calculated for each of these measurements. The current temperature and time is also recorded for each measurement. Plots of the results may be prepared from the stored data and printed at (29) using a Hewlett-Packard 7475A six pen plotter.

The impedance of a resin as measured by its response to an applied oscillating electric field will in general arise from two types of molecular processes—ionic and dipolar.

Using either bridge or time-domain techniques, the real and imaginary components of the material's macroscopic impedance $Z^*$ is determined as a function of frequency. In the formulas below these components are expressed as $C_p$ and $G_p$. Knowledge of the equivalent air filled replaceable capacitance $C_o$ of the measurement circuit allows calculation of the complex permittivity $\epsilon^*$, an intensive property which is independent of the material's size and shape.

$$\epsilon' = \frac{C_p}{C_o} \quad (5)$$

$$\epsilon'' = \frac{G_p}{\omega C_o}$$

Both the real and the imaginary components of $\epsilon^*$ have a dipolar and an ionic component.

$$\epsilon' = \epsilon'd + \epsilon'i$$

$$\epsilon'' = \epsilon''d + \epsilon''i \quad (6)$$

The dipolar component arises from rotational diffusion of molecular dipolar moments. In its simplest form, the polar component's frequency dependence is represented by a single relaxation time $\tau$ and $$\epsilon'd = \frac{\epsilon_o - \epsilon_\infty}{1 + i\omega\tau} + \epsilon_\infty \quad (7)$$

$$\epsilon''d = \frac{(\epsilon_o - \epsilon_\infty) i\omega}{(1 + i\omega\tau)}$$

Where $\epsilon_o$ and $\epsilon_\infty$ are the limiting low and high frequency values of $\epsilon^*$. The rate of rotational diffusion or reorientation of the polar moments is characterized by the relaxation time $\tau$. In most systems, a distribution of relaxation times is observed. The distribution is due to a combination of molecular phenomena, including the presence of more than one polar species, the assymetric shape of the polar group and intra- and intermolecular forces. The intermolecular forces determine the extent to which the motion of the dipoles are correlated with each other. In this case $\epsilon^*_d$ may be represented by $$\frac{\epsilon^* - \epsilon_o}{\epsilon_o - \epsilon_\infty} = \frac{1}{(1 + i\omega\tau)}\beta \quad (8)$$

where $\beta$ is a measure of the distribution in relaxation times.

The presence of ions often dominates the properties of $\epsilon^*$ of resins and their changing electrical properties during the cure process. For example, the presence of mobile ions gives rise to localized layers of charge. Since these layers of charge are separated by very small distances, on the order of $A^\circ$, the corresponding effective capacitance can be extremely large. It is not uncommon to observe values of $\epsilon'$, for example, on the order of $10^6$ in curing or processing resins, compared to values of $\epsilon'$ less than 10 which are common for more typical liquids and solids. Similarly the translational diffusion of ions significantly increases the conductance and thereby gives rise to values of $\epsilon''$ which are equally large, particularly as the frequency decreases.

The magnitude of the electrical impedance of the resin is often strongly dependent on the presence of ions. Many early reports on electrical characterization of the cure process neglected the role of ions. This may be due to the extensive solid state literature on widely used polymers (polyethylene, polyesters, polyamides, etc.) which focuses on these polymers' dipolar properties. I have observed, however, that ionic processes play a major role in determining the impedance during the cure process, particularly at low frequencies.

The literature discussing attempts to develop equivalent circuit and molecular models to represent ionic phenomena is long and complex. Simply summarized, ionic systems involve non-equilibrium and irreversible processes dependent upon types, concentration and mobilities of ions as well as electrode dimensions and discharge conditions. The ionic properties are determined in part by charge diffusion, the hindered translational mobility of the ions in the bulk and their interaction with neighboring charged species. They are also determined by space charge, the build up of charged ionic regions around the electrodes as well as any other material interfaces, and the discharge properties at the material interface. No single or unified representation of all of these effects has been widely accepted. While limited and approximate, one convenient representation of these effects is to consider them together as an effective electrode impedance. In this case:

$$\epsilon'i = C_oZ_o\text{SIN}\left(\frac{\eta\pi}{2}\right) \omega^{-(\eta+1)} \frac{\sigma}{8.85 \times 10^{-14}}^2 \quad (9)$$

where $C_o$ is the replaceable capacitance in Farads, $Z = Z_o(i\omega)^{-\eta}$ is the electrode impedance induced by the ions, and $\eta$ is between 0 and 1. The imaginary part of the ionic component has the form:

$$\epsilon''i = \frac{\sigma}{8.85 \times 10^{-14}\omega} - \quad (10)$$

$$C_oZ_o\text{COS}\left(\frac{\eta\pi}{2}\right) \omega^{-(\eta+1)} \frac{\sigma}{8.85 \times 10^{-14}}^2$$

$\sigma$ is the conductivity (ohm$^{-1}$cm$^{-1}$), an intensive variable, in contrast to conductance $G$(ohm$^{-1}$) which is dependent upon cell and sample size. The first term in equation 10 is due to the DC conductance of ions translating through the medium. The $Z_o$ term is due to electrode impedance effects. This term becomes increasingly significant as the frequency of measurement is decreased.

It is important to remember that any procedure which is developed and used for polymer cure process monitoring is, in general, unique to a particular resin system and/or application. The essential requirement is that the molecular basis for the frequency dependence of the dielectric signal be understood. Using this information, the ionic contribution $\epsilon^*_i$, the dipolar contribution $\epsilon^*_d$ and the magnitude of $\epsilon$ are then used for cure cycle monitoring and control.

I claim:

1. A dielectric probe useful for sensing electrical characteristics of materials in contact with it comprising (a) a substrate having an electrical conductivity no greater than $10^{-7}$ mho/cm$^{-1}$ over a frequency range of use, a loss tangent at one megahertz of less than 0.001, a stable capacitance curve exhibiting little or no hysteresis through the range of 1 herz to 10 megahertz at the temperatures of use, and a known dielectric permittivity of less than 13, and (b) at least two chemically resistant, electrically conductive parallel interdigitated electrodes affixed thereto, the spaces between the digits of the interdigitated electrodes being no greater than about 0.01 inch.

2. A probe of claim 1 wherein the electrodes are affixed in a pectinate interdigitated configuration.

3. A probe of claim 1 wherein the electrodes are made of gold, platinum, titanium, tungsten, palladium, chromium or combinations thereof.

4. A probe of claim 1 wherein the substrate has reproducible capacitance, conductivity, and frequency-responsive characteristics through a temperature range.

5. Probe of claim 1 including two terminal means for each electrode.

6. The probe of claim 1 wherein the substrate is selected from a polyimide, glass, or aluminum oxide.

7. Apparatus for controlling process variables of a medium undergoing chemical or physical change comprising (i) a dielectric probe useful for sensing electrical characteristics of materials in contact with it comprising (a) a substrate having an electrical conductivity no greater than $10^{-7}$ mho/cm$^{-1}$ over a frequency range of use, a loss tangent at one megahertz of less than 0.001, a stable capacitance curve exhibiting little or no hysteresis through the range of 1 herz to 10 megahertz at the temperatures of use, and a known dielectric permittivity of less than 13, and (b) at least two chemically resistant, electrically conductive parallel interdigitated electrodes affixed thereto, the spaces between the digits of the interdigitated electrodes being no greater than about 0.01 inch, (ii) means for generating a control signal as a predetermined function of an electrical characteristic of a medium in contact with said probe, and (iii) means responsive to said control signal for changing at least one process variable affecting said chemical or physical change.

8. Apparatus of claim 7 wherein said control signal generating means is a temperature controller.

9. Apparatus of claim 7 wherein the control signal responsive means is a heating element.

* * * * *